(12) United States Patent
Zucker et al.

(10) Patent No.: US 11,896,423 B2
(45) Date of Patent: Feb. 13, 2024

(54) TIME-VARYING QUANTIFICATION OF CAPACITIVE AND RESISTIVE ARTERIAL BLOOD FLOW

(71) Applicant: Board of Regents of the University of Nebraska, Lincoln, NE (US)

(72) Inventors: Irving H. Zucker, Omaha, NE (US); Ioannis Chatzizisis, Omaha, NE (US); Han-Jun Wang, Omaha, NE (US); Alicia M. Schiller, Bellevue, NE (US); Peter Ricci Pellegrino, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 17/705,588

(22) Filed: Mar. 28, 2022

(65) Prior Publication Data
US 2022/0218301 A1    Jul. 14, 2022

Related U.S. Application Data

(63) Continuation of application No. 16/971,988, filed as application No. PCT/US2019/019110 on Feb. 22, 2019, now Pat. No. 11,317,889.
(Continued)

(51) Int. Cl.
| | |
|---|---|
| *A61B 8/06* | (2006.01) |
| *A61B 90/00* | (2016.01) |
| *A61B 8/04* | (2006.01) |
| *A61B 8/00* | (2006.01) |
| *A61B 5/026* | (2006.01) |
| *A61B 5/022* | (2006.01) |

(52) U.S. Cl.
CPC .............. *A61B 8/06* (2013.01); *A61B 8/04* (2013.01); *A61B 8/4483* (2013.01); *A61B 8/46* (2013.01); *A61B 90/06* (2016.02); *A61B 2090/063* (2016.02)

(58) Field of Classification Search
CPC ........... A61B 8/04; A61B 8/46; A61B 8/4483; A61B 5/02; A61B 5/0205; A61B 5/021; A61B 5/026
See application file for complete search history.

(56) References Cited

U.S. PATENT DOCUMENTS

| | | | |
|---|---|---|---|
| 11,317,889 B2 * | 5/2022 | Zucker | ................. A61B 8/5223 |
| 2007/0293760 A1 | 12/2007 | Schaafsma | |

(Continued)

OTHER PUBLICATIONS

International Preliminary Report on Patentability in International Appln. No. PCT/US2019/019110, dated Aug. 27, 2020, 7 pages.
(Continued)

*Primary Examiner* — Boniface Ngathi
(74) *Attorney, Agent, or Firm* — Fish & Richardson P.C.

(57) ABSTRACT

Technology is described that can be used for continuous measurements of blood pressure and arterial blood flow to automatically derive time-varying estimates of multiple factors pertaining to a patient's vascular system. Such factors can include, but are not limited to, resistive flow, capacitive flow, vascular resistance, and arterial capacitance. Determination of such factors can allow for the meaningful assessment of the control of vascular resistance and capacitance in real time.

14 Claims, 7 Drawing Sheets

Related U.S. Application Data

(60) Provisional application No. 62/633,707, filed on Feb. 22, 2018.

(56) References Cited

U.S. PATENT DOCUMENTS

| | | |
|---|---|---|
| 2012/0123246 A1 | 5/2012 | King et al. |
| 2012/0259189 A1 | 10/2012 | Cohen et al. |
| 2016/0310103 A1 | 10/2016 | Liu et al. |
| 2017/0172518 A1 | 6/2017 | Vallee et al. |
| 2020/0397398 A1 | 12/2020 | Zucker et al. |

OTHER PUBLICATIONS

International Search Report and Written Opinion in International Appln. No. PCT/US2019/019110, dated May 3, 2019, 9 pages.

\* cited by examiner

TIME-VARYING QUANTIFICATION OF CAPACITIVE AND RESISTIVE ARTERIAL BLOOD FLOW

CROSS-REFERENCE TO RELATED APPLICATIONS

This application is a continuation of U.S. application Ser. No. 16/971,988, filed on Aug. 21, 2020, which is a National Stage Application under 35 U.S.C. § 371 of International Application No. PCT/US2019/019110, filed Feb. 22, 2019, which claims priority to U.S. Application Ser. No. 62/633,707, filed on Feb. 22, 2018. The contents of the prior applications are hereby incorporated by reference in their entirety.

STATEMENT AS TO FEDERALLY SPONSORED RESEARCH

Not applicable.

TECHNICAL FIELD

The present disclosure relates to technology and methods for continuous measurements of blood pressure and arterial blood flow to automatically derive time-varying estimates of multiple factors such as vascular resistance and arterial capacitance.

BACKGROUND

Blood flow in an artery facilitates oxygen delivery, but it is effected by a host of systemic and local factors. Some such factors may include, but are not limited to, systemic perfusion pressure, systemic circulating hormones, sympathetic nervous tone, local autoregulatory and metabolic controllers of vascular resistance, and compliance of the artery itself. All of those factors are dynamic.

While arterial blood flow can be measured clinically, this measurement is generally limited to anatomic assessment of the arteries (e.g., the detection of vascular stenosis) as current clinical technology cannot provide more important functional assessments of the vasculature from these measurements.

SUMMARY

The present disclosure describes technology for continuous measurements of blood pressure and arterial blood flow to automatically derive time-varying estimates of multiple factors. Such factors can include, but are not limited to, resistive flow, capacitive flow, vascular resistance, and arterial capacitance. Determination of such factors can allow for the meaningful assessment of the control of vascular resistance and capacitance in real time. The technology described herein has several applications such as, but not limited to, the quantification of sympathetic vascular control, assessment of organ perfusion, and determination of the functional importance of vascular stenoses. Conventional technologies to assess vascular resistance and conductance are not time-varying and rely on manual tuning of the parameters, which is impractical and highly susceptible to error and operator bias.

In one aspect, this disclosure is directed to a method that includes measuring a series of arterial blood pressures of a patient; measuring a series of arterial blood flows of the patient; synchronizing the measured series of arterial blood flows to the measured series of arterial blood pressures; determining intervals of one cardiac cycle or less over which a change in the series of arterial blood pressures is zero, wherein the determined intervals represent intervals over which a net capacitive blood flow is zero and intervals for which a mean of the series of arterial blood flows equals a mean resistive blood flow; and determining a mean vascular resistance for each interval by dividing a mean arterial blood pressure by the mean resistive blood flow.

Such a method may also include one or more of the following features. The method may also include determining a capacitive blood flow by dividing a difference between the measured series of arterial blood flows and the measured series of arterial blood pressures by the mean vascular resistance. The method may also include determining vasculature capacitance by dividing the determined capacitive blood flow by the first derivative of perfusion pressure with respect to time.

In another aspect, this disclosure is directed to a system that is configured to: measure a series of arterial blood pressures of a patient; measure a series of arterial blood flows of the patient; synchronize the measured series of arterial blood flows to the measured series of arterial blood pressures; determine intervals of one cardiac cycle or less over which a change in the series of arterial blood pressures is zero, wherein the determined intervals represent intervals over which a net capacitive blood flow is zero and intervals for which a mean of the series of arterial blood flows equals a mean resistive blood flow; and determine a mean vascular resistance for each interval by dividing a mean arterial blood pressure by the mean resistive blood flow.

In another aspect, this disclosure is directed to a system for analyzing a vasculature of a patient. In some embodiments, the system includes a blood pressure detection device configured to measure a series of arterial blood pressures of the patient; an ultrasonic blood flow velocity detection device configured to measure a series of arterial blood flows of the patient; and one or more processors. In some embodiments, the one or more processors are configured to perform one or more of the following functions: (i) receive the measured series of arterial blood pressures output from the blood pressure detection device; (ii) receive the measured series of arterial blood flows output from the ultrasonic blood flow velocity detection device; (iii) synchronize the measured series of arterial blood flows with the measured series of arterial blood pressures; (iv) identify, from the measured series of arterial blood pressures, intervals of zero net capacitive blood flow comprising one cardiac cycle or less during which a change in the measured series of arterial blood pressures is zero; (v) determine a mean resistive blood flow for each of the intervals, wherein the mean resistive blood flow for each of the intervals equals a mean of the measured series of arterial blood flows for each of the intervals; and (vi) determine a mean vascular resistance for each of the intervals by dividing a mean of the measured arterial blood pressures for each of the intervals by a corresponding mean resistive blood flow of the mean resistive blood flow for each of the intervals.

Such a system for analyzing a vasculature of a patient may optionally include one or more of the following features. The blood pressure detection device may include an indwelling arterial pressure transducer. The blood pressure detection device may include a non-invasive continuous arterial blood pressure detection device. The non-invasive continuous arterial blood pressure detection device may utilize a volume-clamp measuring method. The system may also include a user interface. The system may also include signal conditioning circuitry for conditioning the received outputs of the blood pressure detection device and the ultrasonic blood flow velocity detection device. The signal conditioning circuitry may include low-pass filtering, amplification, and/or isolation.

Certain embodiments described herein may have particular advantages. At present, there are no clinical techniques to assess time-varying vascular capacitance and resistance in an automated manner. Other technologies are not time-varying and rely on manual tuning of the parameters, which is highly susceptible to operator error, bias, and is impractical. Some embodiments described herein leverage the physical relationship between arterial blood flow and blood pressure to derive automated, time-varying measurements of downstream capacitance, resistance, and, where physiologically important, back-pressure by assuming a time-varying two-component Windkessel model (resistor and capacitor in parallel). Moreover, in some cases these physiological quantities may be post-processed to assess adequacy of perfusion pressure, to quantify modulation of vascular resistance and capacitance by different local or systemic vascular control mechanisms, or to estimate the physiological significance of anatomical stenoses.

Other features and advantages of the invention will be apparent from the following detailed description and figures, and from the claims.

DETAILED DESCRIPTION

The present disclosure describes technology and methods for continuous measurement of blood pressure and arterial blood flow, and for automatic derivation of time-varying estimates of multiple physiological factors. Such factors can include, but are not limited to, resistive flow, capacitive flow, vascular resistance, and arterial capacitance. Determination of such factors can allow for the meaningful assessment of the control of vascular resistance and capacitance in real time.

Arterial blood flow is crucial for function of perfused tissue and is controlled by both local and systemic factors. While arterial blood flow can be measured using various techniques, these measurements are of limited utility as they reflect a complex composite of multiple hemodynamic drivers. This complexity obscures relevant physiological factors and obstructs clinicians from gleaning the information that they truly would like to know (e.g., if the perfusion is optimal for organ function, if particular local or systemic factors are optimized for the perfused tissue of interest, how downstream vascular resistance is being regulated, whether arterial elasticity is relatively fixed or dynamic, and the like).

The technology and methods described herein leverage the physical relationship between arterial blood flow and blood pressure to derive automated, time-varying measurements of factors such as, but not limited to, downstream capacitance, resistance, and, where physiologically important, back-pressure by assuming a time-varying two-component Windkessel model (resistor and capacitor in parallel). These physiological quantities may be post-processed to assess adequacy of perfusion pressure, quantify modulation of vascular resistance and capacitance by different local or systemic vascular control mechanisms, estimate back-pressure, and the like.

Figure 1A:
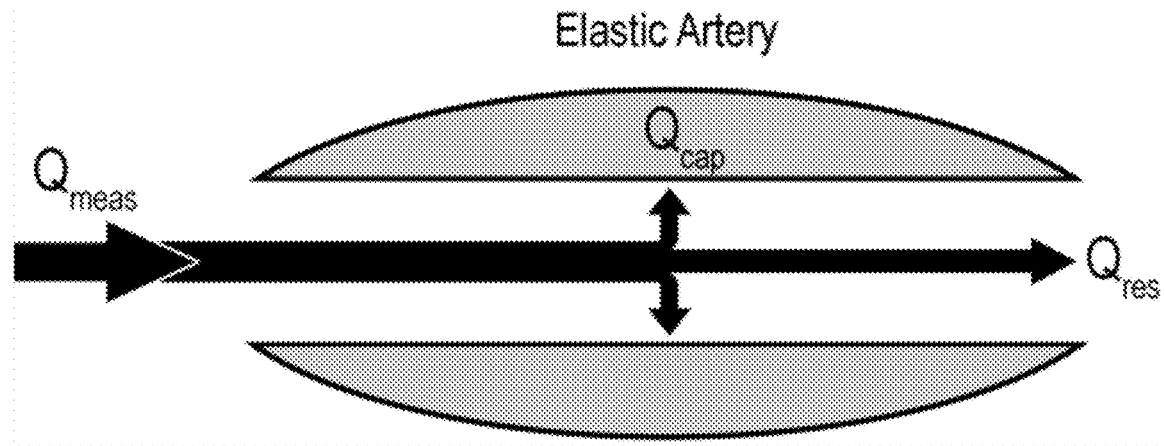
FIG. 1A is a schematic depiction of blood flow through and within an artery.

Turning to the figures, as schematically depicted in FIG. 1A, because arteries are elastic, perfusion pressure can drive blood flow either into the capacitive elastic artery or along the downstream vascular resistance. Measurements of blood flow tend to reflect both the capacitance and the elastance of the vascular bed.

Figure 1B:
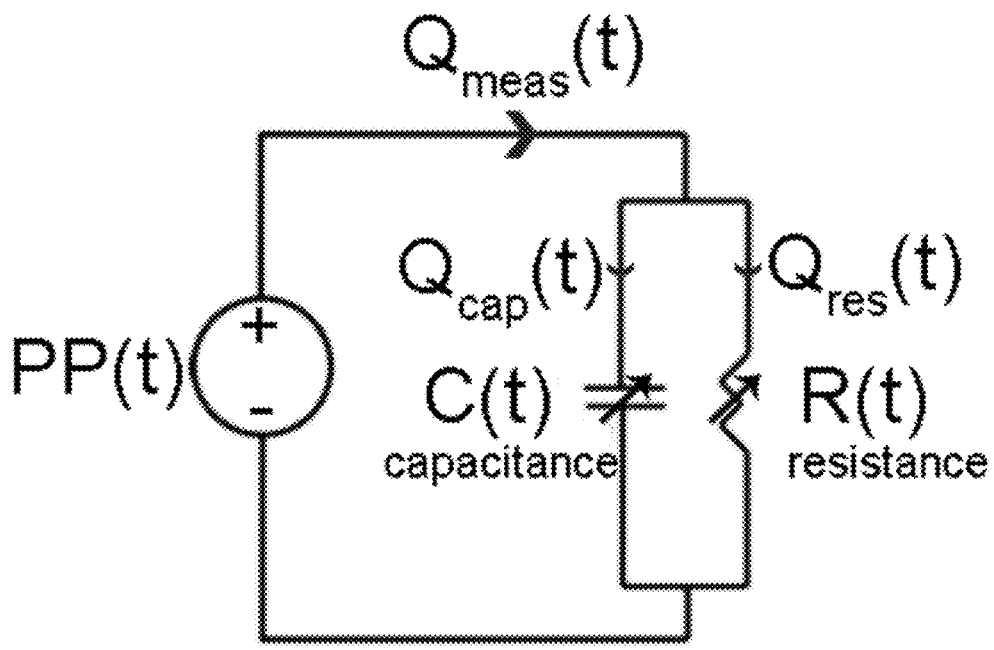
FIG. 1B is a two-component Windkessel model of the circulation in which both the capacitive and resistive components are time-varying.

As depicted in FIG. 1B, this disclosure describes systems and methods that, in some embodiments, use a two-component Windkessel model of the circulation in which both the capacitive and resistive components are time-varying. Accordingly, the two-component Windkessel model can be used to parse arterial blood flow into capacitive flow (i.e., flow into the elastic artery) and resistive flow (i.e. flow along the downstream vascular resistance) by using simultaneous arterial blood pressure measurement.

The time-varying relationships and models can also be represented in the following equations:

Fundamental Definitions of RC Circuit in Parallel (1-3)

$$Q_{meas}(t) = Q_{cap}(t) + Q_{res}(t) \quad (1)$$

$$Q_{res}(t) = R^{-1}(t)P(t) = G(t)P(t) \quad (2)$$

$$Q_{cap}(t) = C(t)\frac{dP(t)}{dt} \quad (3)$$

From Equation 3, $$\int_{t_1}^{t_2} Q_{cap}(t)dt = 0 | \int_{t_1}^{t_2} dP(t)dt = 0$$

Using Equation 1 to substitute for $Q_{cap}(t)$ $$\int_{t_1}^{t_2} Q_{res}(t)dt = \int_{t_1}^{t_2} Q_{meas}(t)dt | \int_{t_1}^{t_2} dP(t)dt = 0$$

where $Q_{meas}$=measured arterial blood flow, $Q_{cap}$=capacitive blood flow, $Q_{res}$=resistive blood flow, R=resistance, P=perfusion pressure, G=admittance, C=capacitance By leveraging the cyclic nature of arterial blood pressure and the fact that net capacitive flow is zero over time intervals over which the change in perfusion pressure is zero, the systems and methods described herein allow for the automated, time-varying estimation of factors such as, but not limited to, resistive flow, resistance, capacitive flow, and capacitance.

Figure 2:
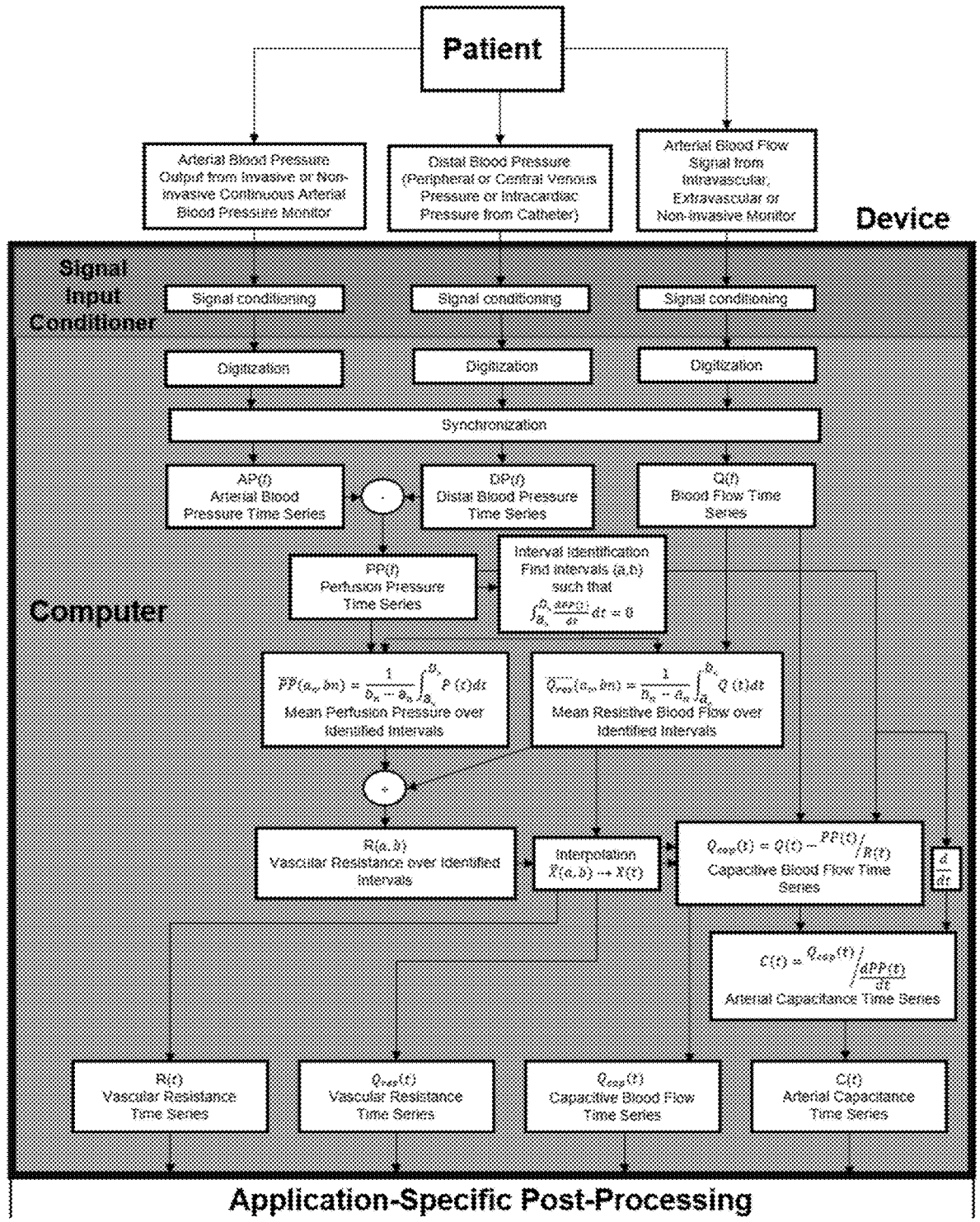
FIG. 2 is a flowchart depicting an example process for continuous measurements of blood pressure and arterial blood flow to automatically derive time-varying estimates of multiple factors.

The general-case flow chart is shown in FIG. 2. First, continuous real-time measurements of arterial blood pressure, arterial blood flow, and, when available, distal pressure (e.g., venous, intracardiac, or intracranial pressure) are made. The arterial blood pressure signal may be measured by an indwelling arterial pressure transducer or by non-invasive means (e.g., volume-clamp method). Distal pressure may be measured via an indwelling central or peripheral venous pressure catheter or, for assessment of the coronary circulation, an intracardiac pressure catheter, or, for assessment of the cerebral circulation, an intracranial (intraparenchymal or intraventricular) pressure transducer. In many cases, distal pressure may be unnecessary or unhelpful, in which case distal pressure can be assumed to be zero. The arterial blood flow or blood flow velocity may be measured either invasively or non-invasively by different techniques (e.g., intravascular Doppler ultrasound wire, noninvasive Doppler ultrasound, transit time ultrasound).

These analog hemodynamic signals are then conditioned so that they are appropriate for digitization by device. This may include low-pass filtering, amplification, and isolation.

The analog hemodynamic signals are then digitized for subsequent digital signal processing.

To account for inherent timing differences in signal acquisition, the system synchronizes the hemodynamic signals to the arterial blood pressure signal. For arterial blood flow, this is done by shifting the arterial blood flow signal by the maximum of the cross-correlation of the arterial blood flow and arterial blood pressure signals. For central venous pressure, the x-descent of the central venous pressure waveform is aligned to the systolic upstroke of the arterial pressure waveform. For peripheral venous pressure, the maximum of the cross-correlation is used to align the signals. Distal atrial cardiac pressures are aligned via the same method as central venous pressure while intraventricular pressures are aligned to the arterial blood pressure waveform by aligning the systolic maxima. Distal intracranial pressures are aligned by aligning the P1 percussion wave from the ICP tracing with the systolic upstroke from the arterial pressure tracing by aligning the maxima of the second derivatives of the aforementioned segments of each signal.

Then, perfusion pressure is obtained by subtracting the synchronized distal blood pressure measurement from the arterial pressure measurement. If no distal blood pressure measurement is made, then perfusion pressure is assumed to be equal to the arterial blood pressure. The user may opt for this assumption even in the presence of a distal pressure measurement (e.g., if the central venous pressure is deemed unreliable by the expert clinician due to improper patient positioning).

Figure 3A:
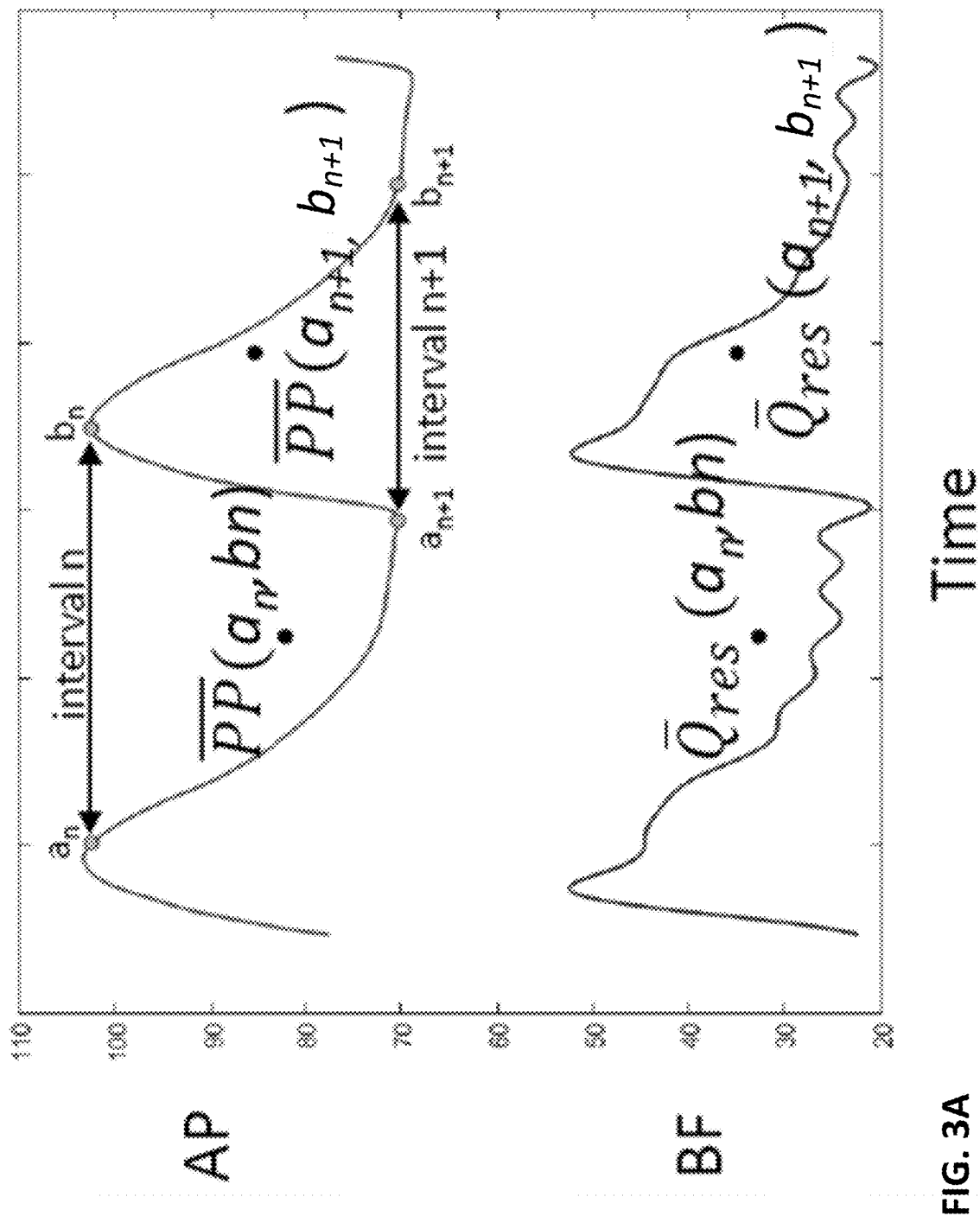
FIGS. 3A-C are time-based graphical representations of arterial blood pressure and blood flow signals for time intervals that are overlapping, contiguous, and disjointed, respectively.
Figure 3B:
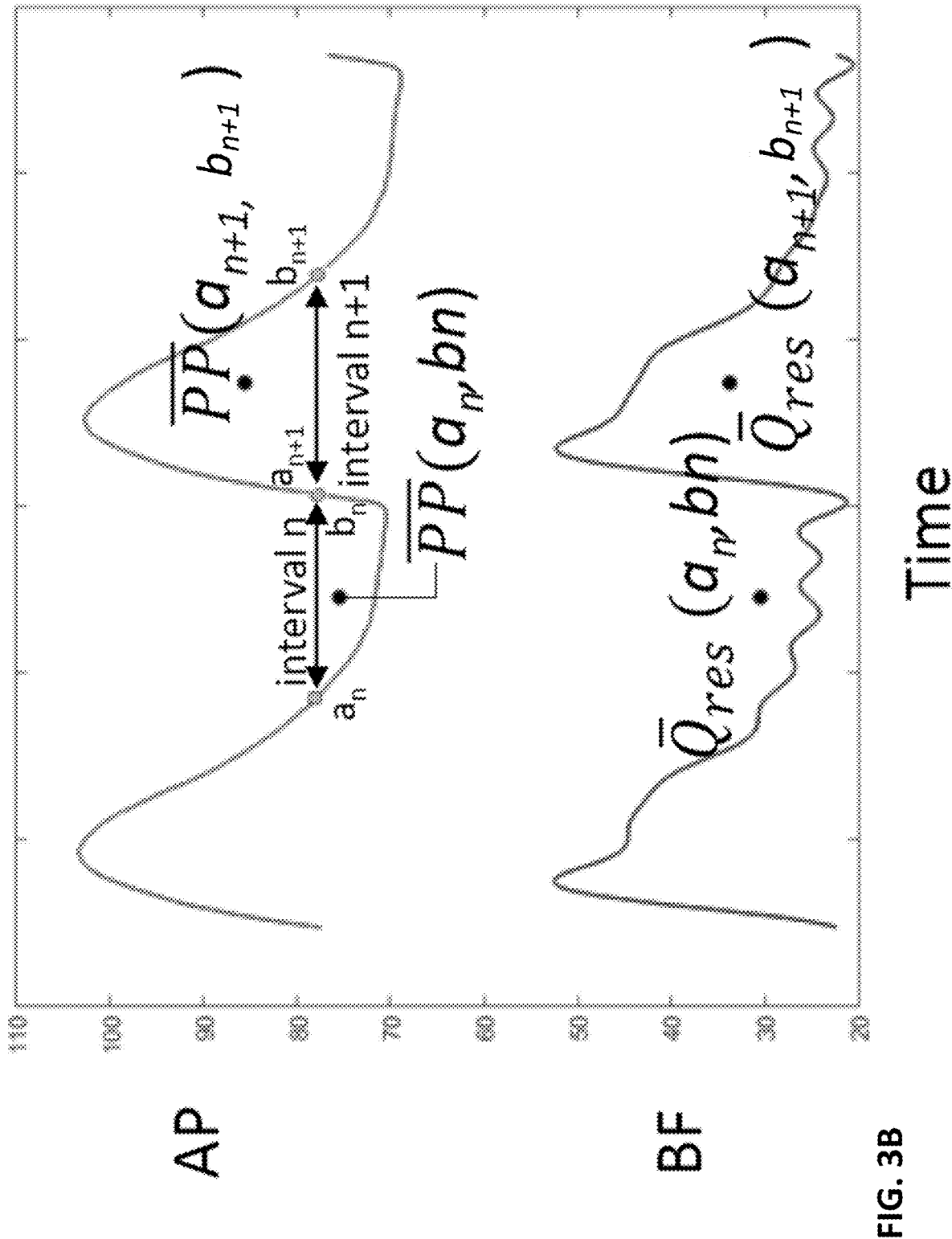
Figure 3C:
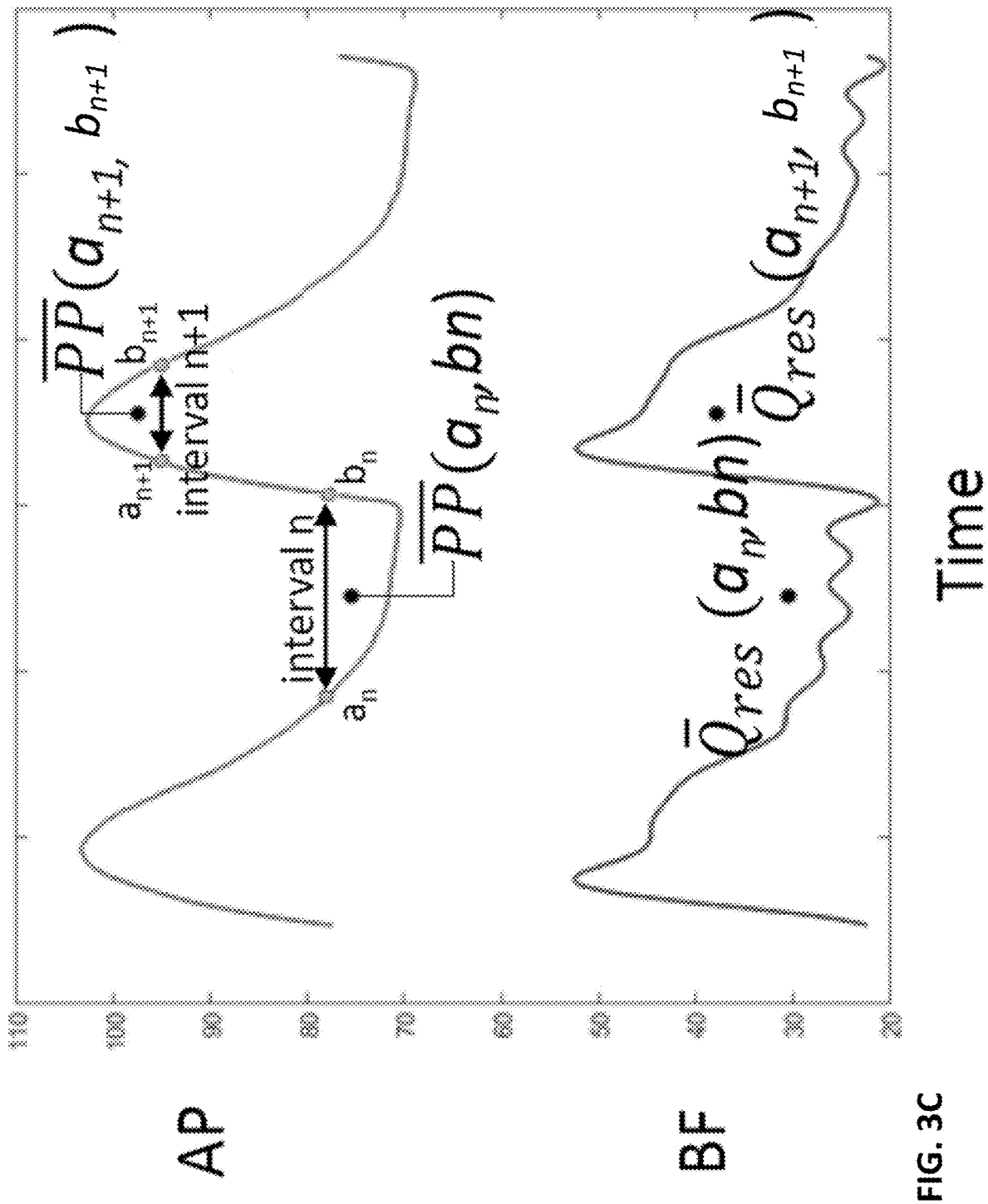

Next, the system uses this perfusion pressure time series to identify short intervals (~1 cardiac cycle or less in length) over which the change in perfusion pressure is equal to zero, which assures that the net capacitive blood flow is equal to zero (proof shown in equations above). Successive intervals may be overlapping (FIG. 3A), contiguous (FIG. 3B), or disjointed (FIG. 3C). "AP" is arterial pressure and "BF" is blood flow.

As the net capacitive blood flow over each identified interval is equal to zero, the mean measured blood flow over each interval is equal to the mean resistive blood flow over each interval. The mean perfusion pressure over the identified intervals is divided by the mean resistive flow to yield mean vascular resistance for each interval.

The mean resistive blood flow and vascular resistance over these intervals are then interpolated (e.g., via linear or cubic interpolation) at the original sampling rate to yield the resistive flow and vascular resistance time series.

The capacitive blood flow is then calculated as the difference between the measured blood flow and the perfusion pressure divided by the vascular resistance. Capacitance is then calculated as the capacitive flow divided by the first derivative of perfusion pressure with respect to time.

The time-varying estimates of resistive blood flow, capacitive blood flow, vascular resistance, and arterial capacitance can then be used, either alone or together with the original perfusion pressure and blood flow data for several clinical implementations. Each of these implementations has unique, implementation-specific post-processing of these signals. For example, for implementations in which modulation of vascular resistance and capacitance are of interest, the time-varying estimates of resistive and capacitive flow may be used for time-varying transfer function analysis with arterial pressure as the input signal for the output resistive flow and the first derivative of arterial pressure with respect to time as the input signal for the output capacitive flow.

Because the automated ability to assess time-varying control of vascular resistance and capacitance gives a powerful window into local and systemic regulators of circulatory control, the technologies and methods described herein have several important potential clinical applications. Some example applications are described below.

Example Implementation for Assessment of Sympathetic Vasomotion

The sympathetic nervous system is an important guardian of body homeostasis that innervates the arteries and veins. But, at present there is no clinically viable way of measuring regional sympathetic vascular control. Because sympathetic vascular control results in a characteristic modulation of vascular resistance (termed sympathetic vasomotion), the technologies and methods described herein greatly advance the ability to quantify sympathetic vascular control, which has important applications to the fields of renal denervation, hemodynamic monitoring, and dysautonomia.

Example Implementation for Assessment of Organ Autoregulation and Adequacy of Perfusion Targeted blood pressure management is a fundamental component of perioperative and critical care, the goal of which is to provide adequate perfusion of a particular organ, usually the brain or kidneys. These target blood pressure ranges are either arbitrarily or empirically defined, and this practice is known to be flawed because of the high degree of patient-to-patient variability in ideal perfusion pressure for these organs. The ideal solution would be to maintain blood pressure in the middle of the autoregulatory range, so that local vascular controllers could distribute blood flow optimally to facilitate ideal organ function. Because autoregulatory mechanisms strongly modulate vascular resistance in a characteristic manner, the technologies and methods described herein can be used to quantify autoregulatory modulation and blood pressure targets to or to warn clinicians when the organ of interest is no longer in the autoregulatory range. This type of personalized approach to blood pressure management would be a huge improvement over current standard of clinical practice and could prevent costly and often lethal sequelae like stroke and acute kidney injury.

Example Implementation for Assessment of Coronary Stenoses

Over the last decade, interventional cardiologists have realized that the addition of functional assessment of coronary stenoses to guide percutaneous coronary interventions improves patient outcomes and prevents unnecessary procedures. These functional assessments are made by administering an intra-arterial bolus of a powerful vasodilator to induce maximal hyperemia and assessing the intravascular pressure drop across the stenosis. Despite compelling data, functional assessment of coronary stenoses has not been widely adopted into clinical practice, largely because the process is time-consuming and potentially harmful. The technologies and methods described herein allows for automated assessment of vascular elastance and resistance which can be performed both proximal and distal to a coronary stenosis to determine the functional significance of the lesion without the need to administer a time-consuming and potentially harmful vasodilator.

Validation Experiments

BACKGROUND: Radiofrequency renal denervation, a promising therapy for hypertension, is currently mired in some controversy. One barrier facing this therapy is the inability to determine or validate whether effective denervation has occurred. Because the renal sympathetic nerves are dynamic controllers of the renal circulation, renal pressure-flow monitoring (as disclosed herein) may provide much-needed intra-procedural feedback. For these validation experiments, the inventors hypothesized that renal pressure-flow time-varying transfer function analysis will demonstrate the elimination of baroreflex-driven, vasoconstrictive renal sympathetic vasomotion after chronic surgical renal denervation in conscious rabbits, and acute functional renal denervation in anesthetized swine.

Figure 4:
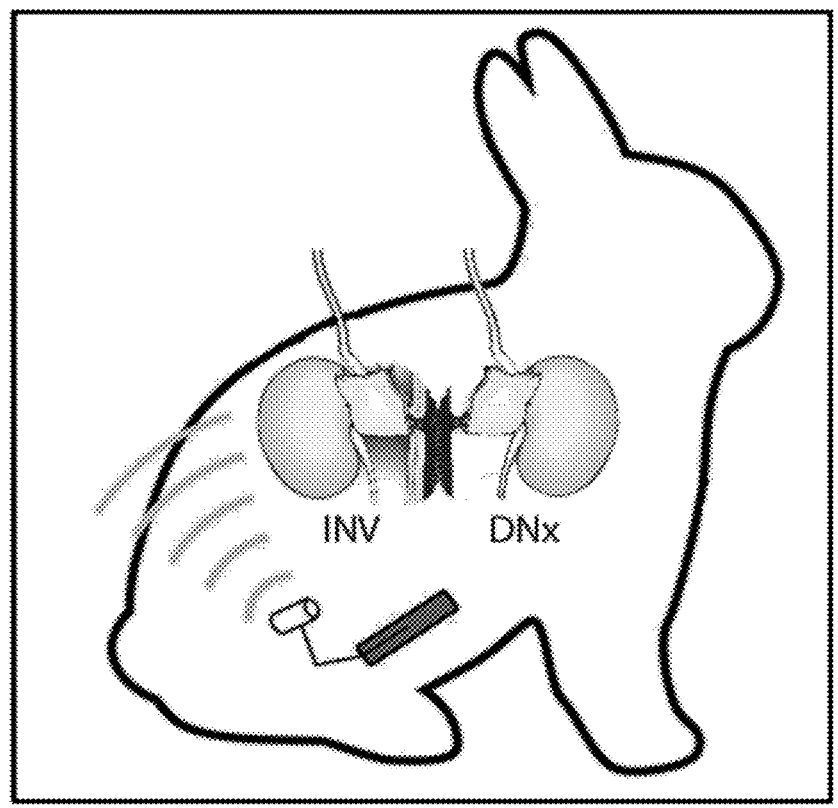
FIG. 4 schematically depicts a validation study involving renal denervation that was performed on rabbits.
Figure 5:
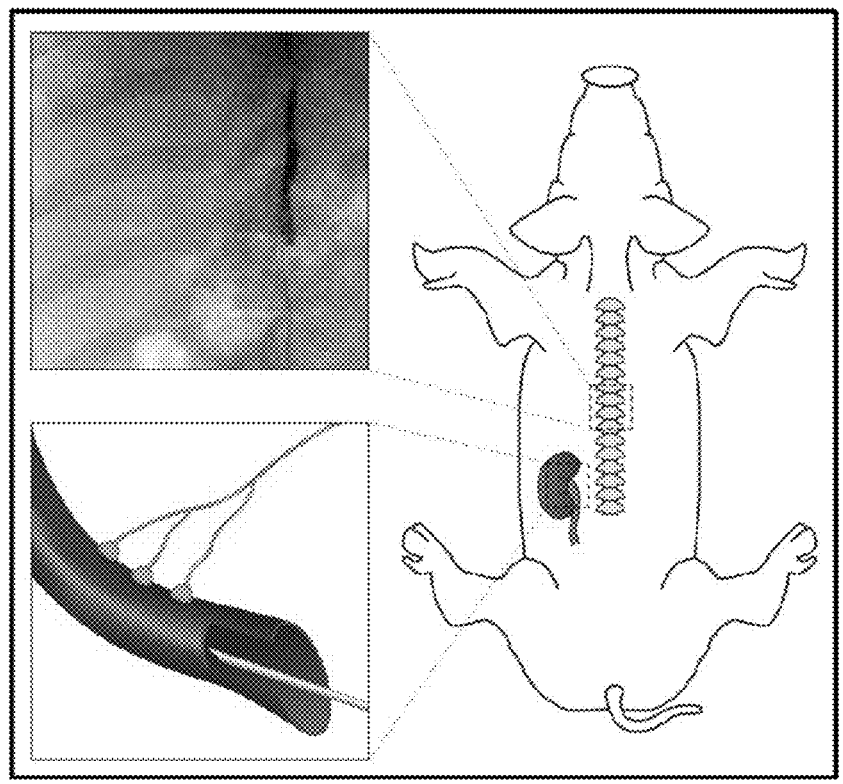
FIG. 5 schematically depicts another validation study involving renal denervation that was performed on swine.

METHODS: Referring to FIG. 4, nine adult male New Zealand White rabbits were implanted with arterial pressure telemeters and bilateral renal flow probes. One kidney of each rabbit was surgically denervated. The rabbits were acclimated to a procedure room and, after a two-week recovery, measurements of arterial pressure and bilateral renal blood flow were obtained in the conscious state. Referring to FIG. 5, ten pigs were induced and then anesthesia was maintained via ketamine-midazolam IV infusion. T9/T10 intrathecal and arterial access were established. A Volcano ComboWire® was placed in the renal artery to measure intravascular pressure and flow velocity. Intrathecal ropivacaine was given to reduce renal sympathetic tone, and renal pressure-flow measurements were repeated.

Figure 6:
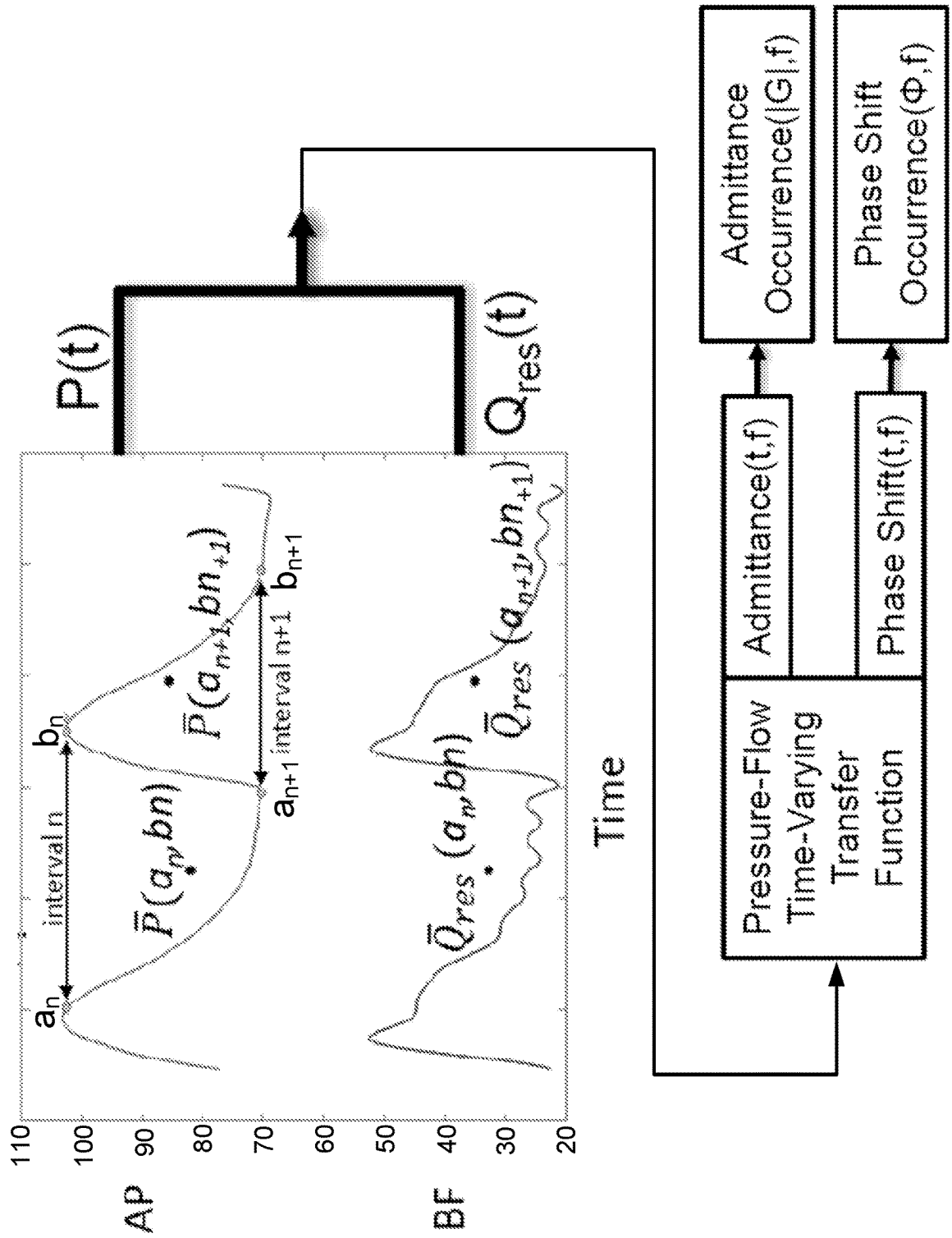
FIG. 6 depicts the high-level workflow associated with the renal pressure-flow time-varying transfer function analysis that was used for the validation studies on the rabbits and swine.

Referring to FIG. 6, Arterial pressure and renal blood flow measurements were used to estimate resistive flow as a function of time, which was in turn used to derive the renal pressure-flow time-varying transfer function (TVTF). TVTF analysis focused on known sympathetic vaso-motor frequencies (0.2-0.75 Hz in rabbits, 0.03-0.1 Hz in pigs). Control of renal vascular resistance in different states of innervation was characterized by occurrence plots of admittance gain and phase shift of the TVTF. Admittance gain reflects the normalized magnitude of oscillations in renal blood flow; phase shift reflects the timing of renal blood flow oscillations relative to arterial pressure.

RESULTS: Table 1 (below) illustrates the mean hemodynamics of the rabbits (with one kidney innervated (INV) and one kidney denervated (DNx)).

TABLE 1

| Parameter | Results |
|---|---|
| Arterial Pressure (mmHg) | 71 +/− 2 |
| Heart Rate (bpm) | 219 +/− 6 |
| INV Renal Blood Flow (mL/min) | 43 +/− 3 |
| DNx Renal Blood Flow (mL/min) | 47 +/− 4 |

The p-value of the above INV Renal Blood Flow and the DNx Renal Blood Flow data was 0.49. Innervated kidneys exhibited more negative phase shift behavior at known sympathetic vasomotor frequencies compared to surgically denervated kidneys.

Table 2 (below) illustrates the mean hemodynamics of the pigs before ("Baseline") and after renal sympatholysis with intrathecal ropivacaine ("Ropi").

TABLE 2

| Parameter | Baseline | Ropi | P-value |
|---|---|---|---|
| Arterial Pressure (mmHg) | 83 +/− 4 | 72 +/− 7 | 0.08 |
| Heart Rate (bpm) | 85 +/− 8 | 71 +/− 5 | 0.03 |
| Renal Blood Flow Velocity (cm/sec) | 24 +/− 3 | 28 +/− 5 | 0.33 |

Prior to renal sympatholysis with intrathecal ropivacaine, the renal pressure-flow time-varying transfer function exhibits more phase asynchrony at known sympathetic vasomotor frequencies.

SUMMARY: Both chronic surgical renal denervation in rabbits and acute functional denervation in swine reduce low admittance gain, negative phase shift behavior of the renal pressure-flow time-varying transfer function. This is consistent with the reduction of an active vasoconstrictive, baroreflex-driven influence on the renal vasculature. This baroreflex-driven, vasoconstrictive behavior revealed by this analysis is renal sympathetic vasomotion, the rhythmic control of the renal vasculature driven by rhythmic renal sympathetic nervous activity. The ability to assess renal sympathetic vasomotion via the renal pressure-flow time-varying transfer function may provide the basis for important intra-procedural feedback for interventionists performing therapeutic renal denervation.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A system for analyzing a vasculature of a patient, the system comprising:
   a blood pressure detection device configured to measure a series of arterial blood pressures of the patient;
   an ultrasonic blood flow velocity detection device configured to measure a series of arterial blood flows of the patient; and
   one or more processors configured to:
      receive the measured series of arterial blood pressures output from the blood pressure detection device;
      receive the measured series of arterial blood flows output from the ultrasonic blood flow velocity detection device;
      synchronize the measured series of arterial blood flows with the measured series of arterial blood pressures; and
      identify, from the measured series of arterial blood pressures, intervals of zero net capacitive blood flow comprising one cardiac cycle or less during which a change in the measured series of arterial blood pressures is zero.

2. The system of claim 1, wherein the one or more processors are further configured to determine a mean resistive blood flow for each of the intervals, wherein the mean resistive blood flow for each of the intervals equals a mean of the measured series of arterial blood flows for each of the intervals.

3. The system of claim 1, wherein the one or more processors are further configured to determine a mean vascular resistance for each of the intervals by dividing a mean of the measured arterial blood pressures for each of the intervals by a corresponding mean resistive blood flow of the mean resistive blood flow for each of the intervals.

4. The system of claim 1, wherein the blood pressure detection device comprises an indwelling arterial pressure transducer.

5. The system of claim 1, wherein the blood pressure detection device comprises a non-invasive continuous arterial blood pressure detection device.

6. The system of claim 5, wherein the non-invasive continuous arterial blood pressure detection device utilizes a volume-clamp measuring method.

7. The system of claim 1, further comprising a user interface.

8. The system of claim 1, further comprising signal conditioning circuitry for conditioning the received outputs of the blood pressure detection device and the ultrasonic blood flow velocity detection device, wherein the signal conditioning circuitry includes low-pass filtering, amplification, and isolation.

9. A method comprising:
   measuring a series of arterial blood pressures of a patient;
   measuring a series of arterial blood flows of the patient;
   synchronizing the measured series of arterial blood flows with the measured series of arterial blood pressures; and
   determining intervals of one cardiac cycle or less over which a change in the measured series of arterial blood pressures is zero.

10. The method of claim 9, wherein the determined intervals represent intervals over which a net capacitive blood flow is zero and intervals for which a mean of the series of arterial blood flows equals a mean resistive blood flow.

11. The method of claim 9, further comprising determining a mean resistive blood flow for each of the intervals, wherein the mean resistive blood flow for each of the intervals equals a mean of the measured series of arterial blood flows for each of the intervals.

12. The method of claim 9, further comprising determining a mean vascular resistance for each of the intervals by dividing a mean of the measured arterial blood pressures for each of the intervals by a corresponding mean resistive blood flow of the mean resistive blood flow for each of the intervals.

13. The method of claim 9, further comprising determining a capacitive blood flow by dividing a difference between the measured series of arterial blood flows and the measured series of arterial blood pressures by mean vascular resistance.

14. The method of claim 13, further comprising determining a vasculature capacitance by dividing the determined capacitive blood flow by a first derivative of perfusion pressure with respect to time.

* * * * *